US010967169B2

(12) United States Patent
Onozuka et al.

(10) Patent No.: US 10,967,169 B2
(45) Date of Patent: Apr. 6, 2021

(54) MEDICAL CONNECTOR, INFUSION SET, AND FLUID COLLECTION METHOD

(71) Applicant: TERUMO KABUSHIKI KAISHA, Tokyo (JP)

(72) Inventors: Toshiko Onozuka, Azumino (JP); Kazuya Akiyama, Showa-cho (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 121 days.

(21) Appl. No.: 16/132,588

(22) Filed: Sep. 17, 2018

(65) Prior Publication Data

US 2019/0015655 A1 Jan. 17, 2019

Related U.S. Application Data

(63) Continuation of application No. PCT/JP2017/007917, filed on Feb. 28, 2017.

(30) Foreign Application Priority Data

Mar. 22, 2016 (JP) .............................. JP2016-056833

(51) Int. Cl.
*A61M 39/26* (2006.01)
*A61M 39/04* (2006.01)
(Continued)

(52) U.S. Cl.
CPC ............ *A61M 39/26* (2013.01); *A61M 39/04* (2013.01); *A61M 39/10* (2013.01); *A61M 39/24* (2013.01);
(Continued)

(58) Field of Classification Search
CPC ...... A61M 39/04; A61M 39/10; A61M 39/24; A61M 39/26; A61M 2039/2466;
(Continued)

(56) References Cited

U.S. PATENT DOCUMENTS 5,098,405 A 3/1992 Peterson et al.
5,348,542 A 9/1994 Ellis
(Continued)

FOREIGN PATENT DOCUMENTS

CN 1187139 A 7/1998
CN 1950126 A 4/2007
(Continued)

OTHER PUBLICATIONS

International Search Report with English language translation and Written Opinion issued in International Application No. PCT/JP2017/007917 dated May 30, 2017.
(Continued)

*Primary Examiner* — Manuel A Mendez
*Assistant Examiner* — Justin L Zamory
(74) *Attorney, Agent, or Firm* — Foley & Lardner LLP

(57) ABSTRACT

A medical connector includes: a body member that partitions a flow path between a proximal side opening and a distal side opening; and a male connector connection portion including: a valve body facing the flow path, and a male connector connection port openable and closable by the valve body. The body member comprises a male connector housing portion configured to house a distal end portion of a male connector connected to the male connector connection portion. The male connector housing portion is configured to cause the male connector to communicate with the distal side opening and to prevent inflow of a fluid from the proximal side opening to the male connector housing portion by connection of the male connector to the male connector connection portion.

8 Claims, 6 Drawing Sheets

(51) Int. Cl.
*A61M 39/10* (2006.01)
*A61M 39/24* (2006.01)
*A61M 5/14* (2006.01)

(52) U.S. Cl.
CPC ....... *A61M 5/14* (2013.01); *A61M 2039/2426* (2013.01); *A61M 2039/2433* (2013.01)

(58) Field of Classification Search
CPC ............ A61M 2039/2433; F16K 15/00; F16K 15/026; F16K 15/028; F16K 15/031
See application file for complete search history.

(56) References Cited

U.S. PATENT DOCUMENTS

| | | |
|---|---|---|
| 5,356,396 A | 10/1994 | Wyatt et al. |
| 5,810,768 A * | 9/1998 | Lopez .................. A61M 39/02 604/500 |
| 2012/0330277 A1 | 12/2012 | Winsor et al. |

FOREIGN PATENT DOCUMENTS

| | | |
|---|---|---|
| CN | 102131536 A | 7/2011 |
| CN | 102686254 A | 9/2012 |
| JP | 4-303462 A1 | 10/1992 |
| JP | H04-303466 A | 10/1992 |
| JP | 11-507275 A | 6/1999 |

OTHER PUBLICATIONS

Office Action dated Jul. 3, 2020 for corresponding Chinese Patent Application No. 201780016214.

* cited by examiner

MEDICAL CONNECTOR, INFUSION SET, AND FLUID COLLECTION METHOD

CROSS-REFERENCE TO RELATED APPLICATIONS

This is a bypass continuation of PCT Application No. PCT/JP2017/007917, filed on Feb. 28, 2017, which claims priority to Japanese Application No. 2016-056833, filed on Mar. 22, 2016. The contents of these applications are hereby incorporated by reference in their entireties.

BACKGROUND

The present disclosure relates to a medical connector having a male connector connection portion. In addition, the present disclosure relates to an infusion set formed of a plurality of parts to constitute a part or the whole of an infusion device and including such a medical connector. Further, the present disclosure relates to a fluid collection method using such a medical connector.

Conventionally, medical connectors for connection of tubular bodies have been used in infusion devices and the like that supply fluids such as a medical solution to a living body such as a patient. In addition, as the medical connector, there is also known a medical connector including: a body member that partitions a flow path between a proximal side opening and a distal side opening; and a male connector connection portion that has a male connector connection port which can be opened and closed by a valve body facing the flow path. A medical connector used in an infusion device is described in, for example, JP 2005-334280 A.

SUMMARY

FIG. 10 of JP 2005-334280 A describes the infusion device in which an infusion container, a drip tube, a medical connector, an indwelling needle, and the like are disposed in this order from a proximal side to a distal side and connected by a tube.

Using such an infusion device, when it becomes necessary to collect a fluid such as blood from the living body for a blood test or the like when a needle is indwelled in the living body, a medical device such as a syringe for fluid collection is prepared, and a male connector connected to the medical device is connected to a male connector connection portion of the medical connector to suck the fluid into the male connector.

Then, it is necessary to suck the fluid only from a distal side (indwelling needle side) without sucking the fluid from a proximal side (infusion container side) at this time. Thus, in the conventional infusion device, it is necessary to collect fluid by providing a one-touch clamp on the proximal side of the medical connector and operating this clamp at the time of collecting a fluid to prevent inflow of the fluid from the proximal side.

Certain embodiments described in this disclosure have been developed in view of such inconvenience, and an object thereof is to provide a medical connector, an infusion set, and a fluid collection method capable of facilitating collection of a fluid into a male connector.

A medical connector according to one embodiment includes: a body member that partitions a flow path between a proximal side opening and a distal side opening; and a male connector connection portion that has a valve body facing the flow path and a male connector connection port openable and closable by the valve body. The body member includes a male connector housing portion configured to house a distal end portion of a male connector connected to the male connector connection portion. The male connector housing portion is configured to cause the male connector to communicate with the distal side opening and to prevent inflow of a fluid from the proximal side opening to the male connector housing portion by connection of the male connector to the male connector connection portion.

In one aspect, the male connector housing portion is provided with a check valve which allows the inflow of the fluid from the proximal side opening to the male connector housing portion and prevents inflow of the fluid from the male connector housing portion to the proximal side opening, and the check valve is configured to prevent the inflow of the fluid from the proximal side opening to the male connector housing portion by a pressing force from the male connector when the male connector is connected to the male connector connection portion.

In one aspect, the male connector housing portion includes a valve seat, and the check valve is an elastic valve configured to seat on the valve seat, and is configured to allow the inflow of the fluid from the proximal side opening to the male connector housing portion via a space between the valve seat and the check valve.

In one aspect, the check valve has a slit and is configured to allow the inflow of the fluid from the proximal side opening to the male connector housing portion via the slit.

In one aspect, the male connector housing portion includes a communicating hole that causes the male connector housing portion and the proximal side opening to communicate with each other, and the communicating hole is configured to be closed by the male connector when the male connector is connected to the male connector connection portion.

In one aspect, the medical connector is provided with a check valve, which allows inflow of the fluid from the proximal side opening to the communicating hole and prevents inflow of the fluid from the communicating hole to the proximal side opening, between the communicating hole and the proximal side opening.

In one aspect, the valve body and the check valve are integrally formed.

In another embodiment, an infusion set includes a plurality of parts that constitute a part or the whole of an infusion device that supplies a fluid to a living body, and includes the medical connector as described above.

In another embodiment, a fluid collection method for collecting a fluid from a flow path of a medical connector includes: providing a medical connector including: a body member that partitions the flow path between a proximal side opening and a distal side opening; and a male connector connection portion that has a valve body facing the flow path and a male connector connection port openable and closable by the valve body; connecting a male connector to the male connector connection portion; causing the male connector to communicate with the distal side opening and preventing inflow of the fluid from the proximal side opening to the male connector by the connection of the male connector to the male connector connection portion; and collecting the fluid from the distal side opening into the male connector.

According to certain embodiment described in this disclosure, it is possible to cause the male connector to communicate with the distal side opening and to prevent the inflow of the fluid from the proximal side opening to the male connector housing portion by the connection of the male connector to the male connector connection portion, and thus, it is possible to start collecting the fluid only by connecting the male connector to the male connector connection portion.

Therefore, it is possible to provide the medical connector, the infusion set, and the fluid collection method capable of facilitating the collection of the fluid into the male connector.

DETAILED DESCRIPTION

Hereinafter, a medical connector 1 according to an embodiment of the present disclosure will be illustrated and described in detail with reference to FIGS. 1 to 4.

Figure 1:
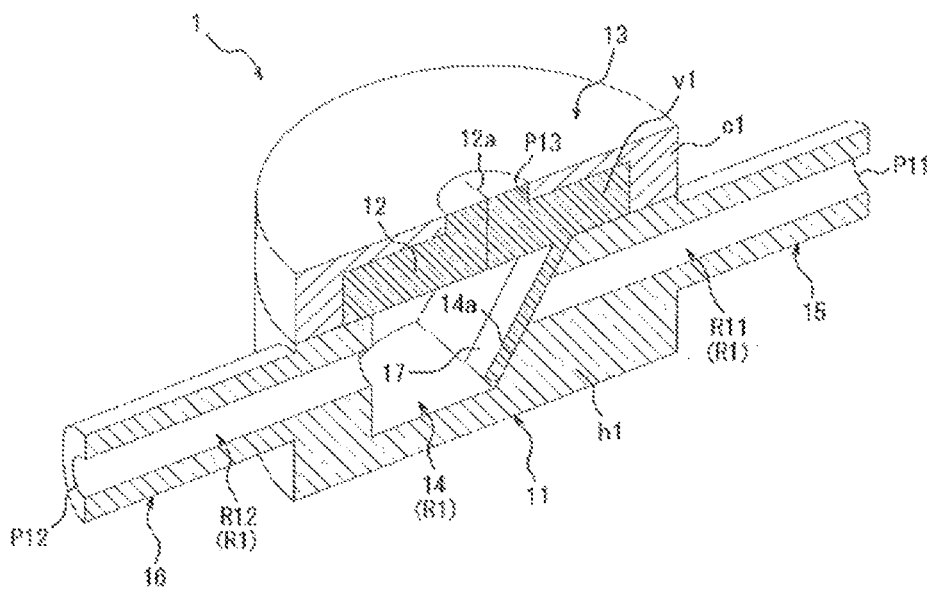
FIG. 1 is a cross-sectional perspective view of a medical connector according to one embodiment of the present invention.
Figure 2:
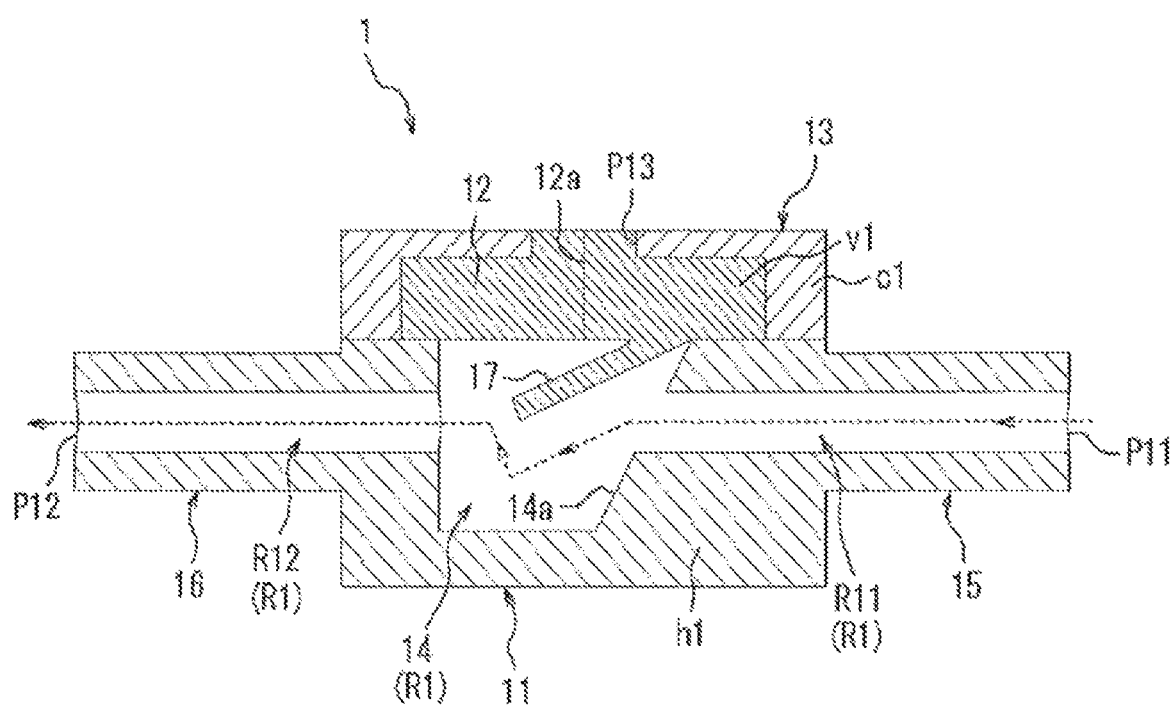
FIG. 2 is a cross-sectional view illustrating a state at the time of supplying a fluid to a living body when the medical connector of FIG. 1 is used in an infusion device.
Figure 3:
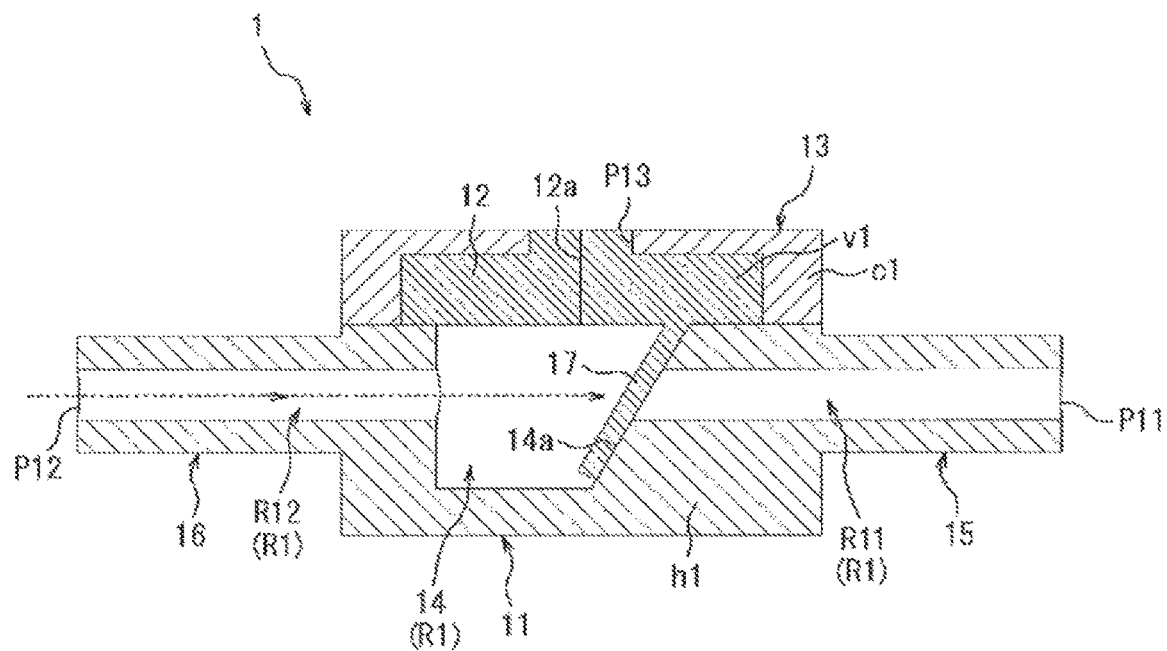
FIG. 3 is a cross-sectional view illustrating a state at the time of stopping supply of a fluid to a living body when the medical connector of FIG. 1 is used in the infusion device.
Figure 4:
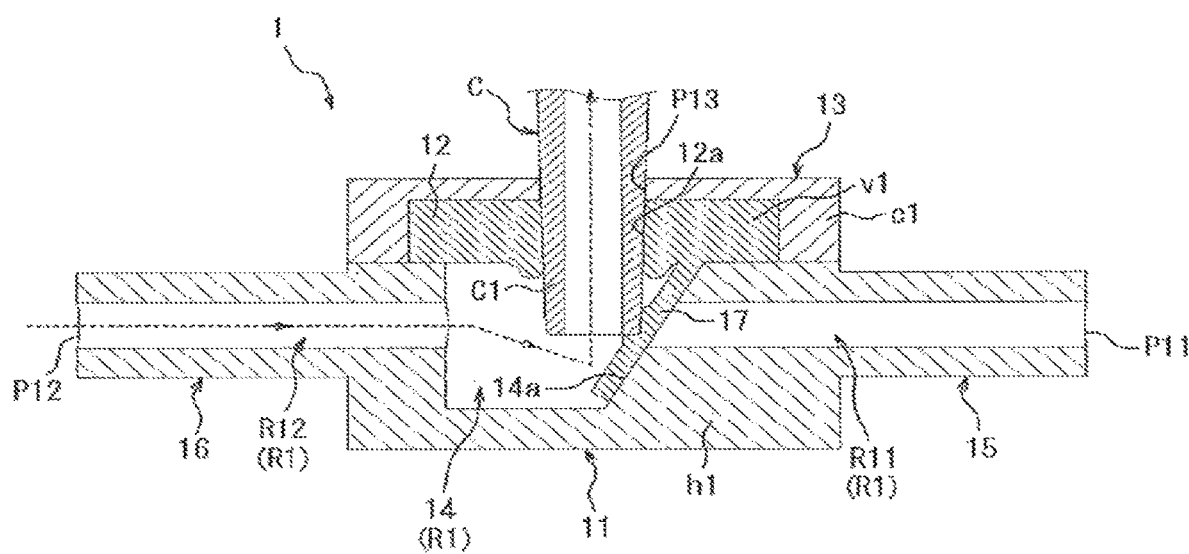
FIG. 4 is a cross-sectional view illustrating a state at the time of collecting a fluid from a living body when the medical connector of FIG. 1 is used in the infusion device.

FIG. 1 illustrates the medical connector 1 of the present embodiment. FIG. 1 illustrates only a portion on a first side of a cross section of the medical connector 1, but a portion on a second side is configured to be symmetric with the portion on the first side. In addition, FIGS. 2 to 4 illustrate states in the case of using the medical connector 1, for example, in an infusion device that supplies a fluid such as a medical solution and a saline solution to a living body such as a patient. FIG. 2 illustrates the state at the time of supplying the fluid to the living body, FIG. 3 illustrates the state at the time of stopping supply of the fluid to the living body, and FIG. 4 illustrates the state at the time of collecting a fluid such as blood from the living body.

As illustrated in FIG. 1, the medical connector 1 includes: a body member 11 that partitions a flow path R1 (see FIG. 2) between a proximal side opening P11 and a distal side opening P12; and a male connector connection portion 13 that has a male connector connection port P13 that can be opened and closed by a valve body 12 facing the flow path R1. In addition, the body member 11 includes a male connector housing portion 14 configured to house a distal end portion C1 of a male connector C (see FIG. 4) connected to the male connector connection portion 13. Here, the flow path R1 is constituted by a proximal side flow path R11 between the proximal side opening P11 and the male connector housing portion 14, the male connector housing portion 14, and a distal side flow path R12 between the male connector housing portion 14 and the distal side opening P12.

In addition, the medical connector 1 includes: a proximal side connection portion 15 that has the proximal side opening P11 and has a tubular shape (for example, a cylindrical shape) configured to be connected to a tube body, for example, a tube, a connector, or the like to an outer peripheral surface thereof; and a distal side connection portion 16 that has the distal side opening P12 and has a tubular shape (for example, a cylindrical shape) configured to be connected to a tube body, for example, a tube, a connector, or the like to an outer peripheral surface thereof.

The male connector connection port P13 has a cylindrical shape that enables connection with the male connector C configured as a male luer of, for example, a lure slip type, a luer lock type, or the like. An engaging portion with the male connector C, made of a male screw or the like configured to fix the luer lock-type male luer may be provided on the outer peripheral surface of the male connector connection portion 13.

The valve body 12, which can open and close the male connector connection port P13, is an elastic slit valve that is positioned at the center of the male connector connection port P13 and has a slit 12a penetrating the front and back of the valve body 12, and is configured such that the slit 12a is opened by the connection of the male connector C to the male connector connection port P13, as a portion surrounding the slit 12a is fixed to the male connector connection portion 13. Incidentally, the slit 12a has a straight-line shape in the present embodiment, but it is also possible to adopt a radial shape such as a cross shape and a Y-shape, or another shape.

The male connector housing portion 14 is provided with a check valve 17. The check valve 17 is an elastic valve configured to seat on a valve seat 14a provided in the male connector housing portion 14, and is configured to allow inflow of the fluid from the proximal side opening P11 to the male connector housing portion 14 via a space between the valve seat 14a and the check valve 17 as illustrated in FIG. 2. In addition, the check valve 17 is configured to prevent inflow of the fluid from the male connector housing portion 14 to the proximal side opening P11 as illustrated in FIG. 3. That is, the check valve 17 is provided in the flow path R1 between the male connector connection port P13 and the proximal side opening P11.

Further, the check valve 17 is configured to prevent the inflow of the fluid from the proximal side opening P11 to the male connector housing portion 14 by a pressing force from the male connector C when the male connector C has been connected to the male connector connection portion 13 as illustrated in FIG. 4. Here, it is preferable that the check valve 17 be configured to prevent the inflow of the fluid by abutting on the distal end portion C1 of the male connector C as illustrated in FIG. 4. However, in place of such a configuration, it is also possible to configure the check valve 17 such that, for example, the inflow of the fluid is prevented by abutment on a portion of the valve body 12 pushed into the male connector C.

Further, the valve seat 14a surrounding an opening end of the proximal side flow path R11 to the male connector housing portion 14 has a planar shape that is inclined from the proximal side to the distal side from a side where the valve body 12 is disposed toward the opposite side. In addition, the check valve 17 is configured as a cantilever valve in which an end portion on the side where the valve body 12 is disposed is fixed with respect to the valve seat 14a and an end portion on the opposite side is a free end. Further, the check valve 17 is configured to block the flow path by being pressed against the valve seat 14a as a portion on the free end side abuts the distal end portion C1 of the male connector C when the male connector C has been connected to the male connector connection portion 13. Incidentally, the valve seat 14a is formed in a planar shape in the present embodiment, but it is also possible to adopt other shapes such as a curved shape.

In addition, the medical connector 1 is configured as a T-shaped connector in which a center axis line of the tubular proximal side connection portion 15 and a center axis line of the tubular distal side connection portion 16 extend in the same direction and a center axis line of the male connector connection port P13 is disposed to be perpendicular to such a direction.

The medical connector 1 is constituted by a housing h1 made of, for example, resin, a cap c1 made of, for example, resin, and a valve member v1 made of, for example, rubber in the present embodiment. The housing h1 and the cap c1 are joined to each other with the valve member v1 sandwiched therebetween.

Here, the body member 11, the proximal side connection portion 15, the distal side connection portion 16, and the male connector housing portion 14, which are described above, are parts of the housing h1. In addition, the male connector connection portion 13 is a part of the cap c1. Further, the valve body 12 and the check valve 17 are parts of the valve member v1. In this manner, the check valve 17 is integrally formed with the valve body 12 which closes the male connector connection port P13.

When being used in the infusion device, the medical connector 1 configured as described above can operate as follows. First, the check valve 17 is opened by the pressure of the fluid on the proximal side positioned on the infusion container side as illustrated in FIG. 2 at the time of supplying the fluid to the living body, and thus, the fluid can flow from the proximal side opening P11 to the distal side opening P12 through the flow path R1. Therefore, it is possible to supply the fluid from the infusion container to the living body through the medical connector 1.

In addition, even if the pressure of the fluid on the distal side positioned on the living body side is increased as illustrated in FIG. 3 at the time of stopping the supply of the fluid to the living body, this pressure is applied in a direction to close the check valve 17, and thus, the inflow of the fluid from the male connector housing portion 14 to the proximal side opening P11 is prevented. Therefore, occurrence of reverse flow of the fluid from the living body into the infusion device is prevented at the time of stopping the supply of the fluid, safety is secured, and occurrence of occlusion in the infusion device is prevented.

Further, when a medical device such as a syringe is prepared for fluid collection and the male connector C connected to this medical device is connected to the male connector connection portion 13 at the time of collecting the fluid from the living body as illustrated in FIG. 4, the portion of the check valve 17 on the free end side is pressed against the valve seat 14a having the inclined planar shape by the distal end portion C1 of the male connector C, and thus, a closed state of the check valve 17 and a communicating state between the male connector C and the distal side opening P12 are secured. Therefore, it is possible to collect the fluid only from the living body by preventing the inflow of the fluid from the infusion container.

As described above, the medical connector 1 of the present embodiment is configured such that the male connector C communicates with the distal side opening P12 and the inflow of the fluid from the proximal side opening P11 to the male connector housing portion 14 is prevented by the connection of the male connector C to the male connector connection portion 13, and thus, it is possible to start collecting the fluid only by connecting the male connector C to the male connector connection portion 13 and to facilitate the collection of the fluid into the male connector C.

In addition, the medical connector 1 of the present embodiment is configured such that the check valve 17 is provided in the male connector housing portion 14, and the check valve 17 prevents the inflow of the fluid from the proximal side opening P11 to the male connector housing portion 14, by the pressing force from the male connector C connected to the male connector connection portion 13, and thus, it is possible to prevent the reverse flow of the fluid from the living body by the check valve 17 and to facilitate the collection of the fluid into the male connector C.

In addition, the medical connector 1 of the present embodiment is configured such that the check valve 17 is provided as the elastic valve configured to seat on the valve seat 14a, and thus, it is possible to prevent the occurrence of reverse flow of the fluid from the living body and to facilitate the collection of the fluid into the male connector C with the simple configuration.

In addition, the medical connector 1 of the present embodiment realizes simplification of the configuration and an assembly process by integrally forming the valve body 12 and the check valve 17.

Next, a medical connector 2 according to another embodiment of the present invention will be illustrated and described in detail with reference to FIGS. 5 to 8.

Figure 5:
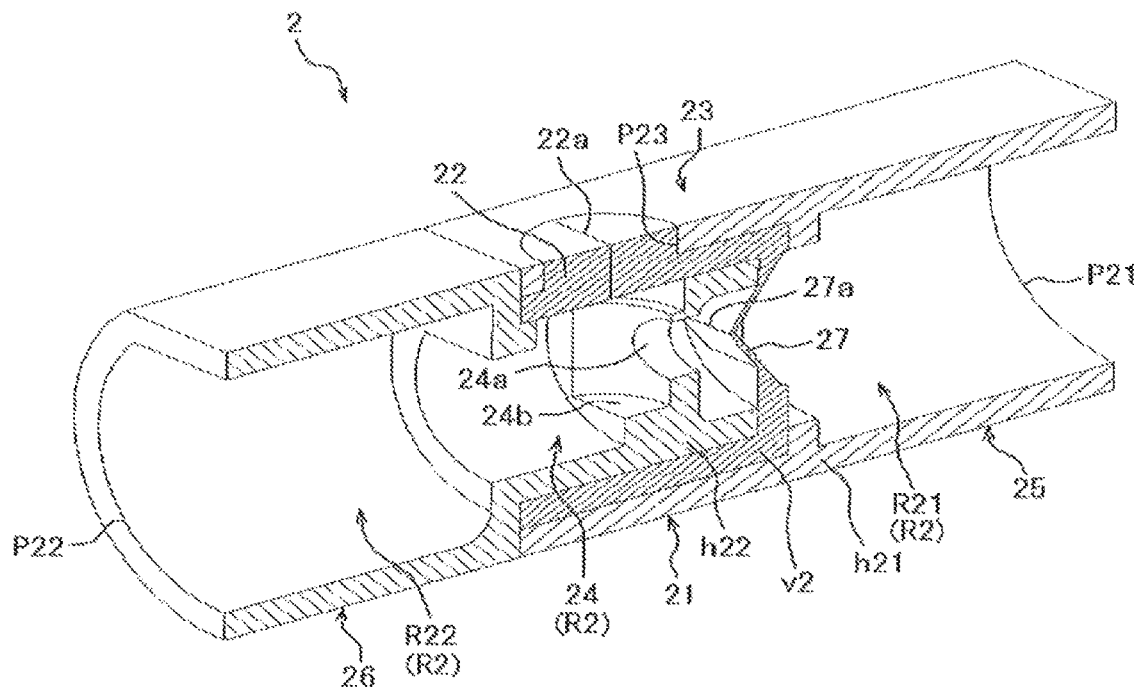
FIG. 5 is a cross-sectional perspective view of a medical connector according to another embodiment of the present invention.
Figure 6:
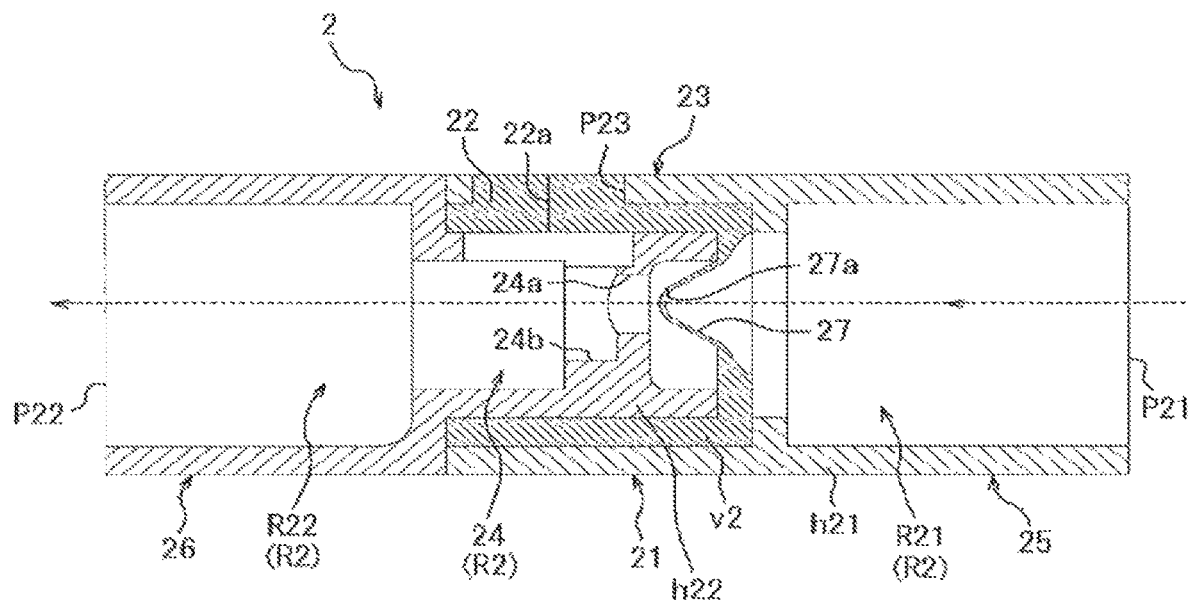
FIG. 6 is a cross-sectional view illustrating a state at the time of supplying a fluid to a living body when the medical connector of FIG. 5 is used in the infusion device.
Figure 7:
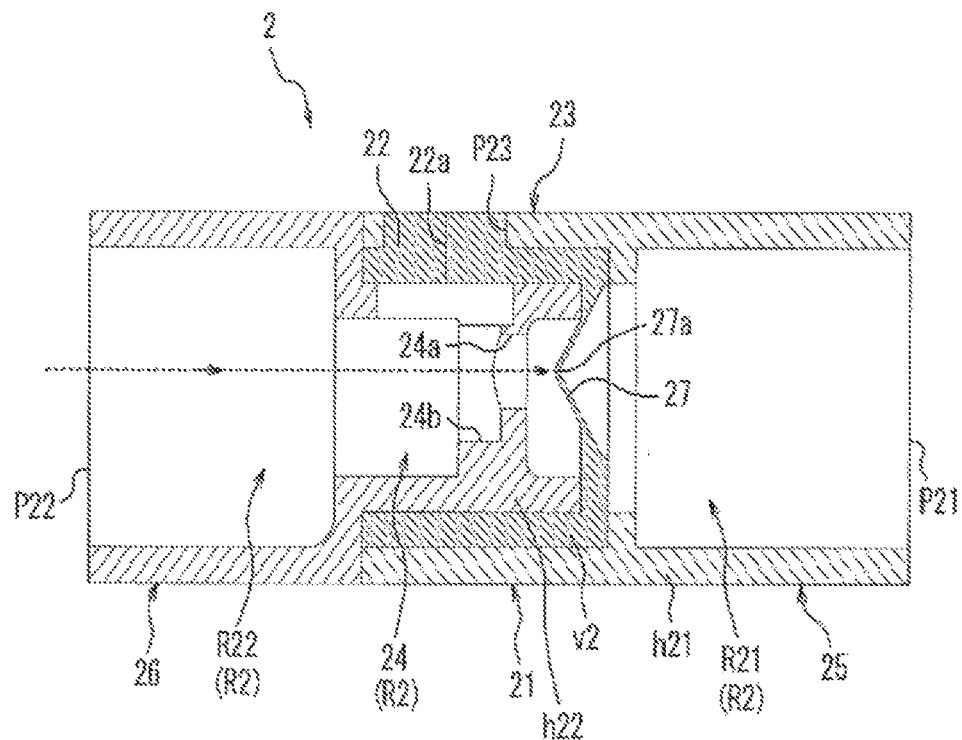
FIG. 7 is a cross-sectional view illustrating a state at the time of stopping supply of a fluid to a living body when the medical connector of FIG. 5 is used in the infusion device.
Figure 8:
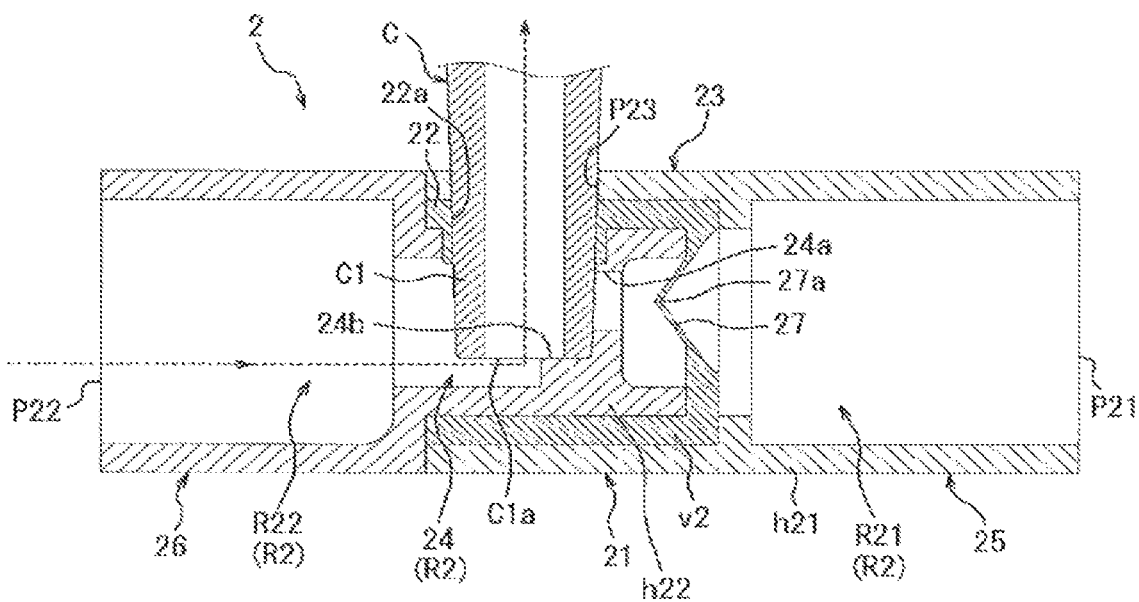
FIG. 8 is a cross-sectional view illustrating a state at the time of collecting a fluid from a living body when the medical connector of FIG. 5 is used in the infusion device.

FIG. 5 illustrates the medical connector 2 of the present embodiment. FIG. 5 illustrates only a portion on a first side of a cross section of the medical connector 2, but a portion on a second side is configured to be symmetric with the portion on the first side. In addition, FIGS. 6 to 8 illustrate states in the case of using the medical connector 2 in an infusion device that supplies a fluid to a living body. FIG. 6 illustrates the state at the time of supplying a fluid to the living body, FIG. 7 illustrates the state at the time of stopping supply of a fluid to the living body, and FIG. 8 illustrates the state at the time of collecting a fluid from the living body.

As illustrated in FIG. 5, the medical connector 2 includes: a body member 21 that partitions a flow path R2 (see FIG. 6) between a proximal side opening P21 and a distal side opening P22; and a male connector connection portion 23 that has a male connector connection port P23 which can be opened and closed by a valve body 22 facing the flow path R2. In addition, the body member 21 includes a male connector housing portion 24 configured to house a distal end portion C1 of a male connector C (see FIG. 8) connected to the male connector connection portion 23. Here, the flow path R2 is constituted by a proximal side flow path R21 between the proximal side opening P21 and the male connector housing portion 24, the male connector housing portion 24, and a distal side flow path R22 between the male connector housing portion 24 and the distal side opening P22.

In addition, the medical connector 2 includes: a proximal side connection portion 25 that has the proximal side opening P21 and has a tubular shape configured to be connected to a tube body, for example, a tube, a connector, or the like to an inner peripheral surface or an outer peripheral surface thereof; and a distal side connection portion 26 that has the distal side opening P22 and has a tubular shape configured to be connected to a tube body, for example, a tube, a connector, or the like to an inner peripheral surface or an outer peripheral surface thereof.

The male connector connection port P23 has a cylindrical shape that enables connection with the male connector C configured as a lure slip-type male luer. The valve body 22, which can open and close the male connector connection port P23, is an elastic slit valve that is positioned at the center of the male connector connection port P23 and has a slit 22a penetrating the front and back of the valve body 22, and is configured such that the slit 22a is opened by the connection of the male connector C to the male connector connection port P23, as a portion surrounding the slit 22a is fixed to the male connector connection portion 23. Incidentally, the slit 22a has a straight-line shape in the present embodiment, but it is also possible to adopt a radial shape such as a cross shape and a Y-shape, or another shape.

The male connector housing portion 24 has a communicating hole 24a that causes the male connector housing portion 24 and the proximal side opening P21 to communicate with each other, and the communicating hole 24a is configured to be closed by the male connector C when the male connector C is connected to the male connector connection portion 23 as illustrated in FIG. 8. The communicating hole 24a has a cylindrical shape and is disposed such that a center axis line thereof is orthogonal to a center axis line of the male connector C connected to the male connector connection portion 23.

In addition, the male connector housing portion 24 includes a step portion 24b on which a distal end surface C1a of the male connector C connected to the male connector connection portion 23 can abut. The step portion 24b is configured to secure a communicating state between the male connector C and the distal side opening P22 when the distal end surface C1a of the male connector C abuts the step portion 24b.

However, the male connector housing portion 24 may include an inclined surface, for example, on which the distal end surface C1a of the male connector C connected to the male connector connection portion 23 can abut instead of including the step portion 24b. In addition, when the male connector C connected to the male connector connection portion 23 is a male luer whose diameter decreases toward a distal end, the male connector C may be configured to be locked by the male connector connection port P23 at a position where the communicating state between the male connector C and the distal side opening P22 is secured.

A check valve 27, which allows inflow of the fluid from the proximal side opening P21 to the communicating hole 24a and prevents inflow of the fluid from the communicating hole 24a to the proximal side opening P21, is provided on the proximal side flow path R21 (that is, between the communicating hole 24a and the proximal side opening P21). That is, the check valve 27 is provided in the flow path R2 between the male connector connection port P23 and the proximal side opening P21. In the present embodiment, the check valve 27 has a slit 27a having a straight-line shape, and is configured as a duckbill valve that allows inflow of the fluid from the proximal side opening P21 to the male connector housing portion 24 via the slit 27a.

However, the check valve 27 may be configured as an umbrella valve that has a slit having a straight-line shape, a slit having a radial shape such as a cross shape and a Y-shape, or a slit having another shape at a distal end portion of a conical body having, for example, a conical shape, a geometrical pyramid shape, or the like protruding from the proximal side to the distal side, but may be configured as a valve having another configuration.

In addition, the medical connector 2 is configured as a T-shaped connector in which a center axis of the tubular proximal side connection portion 25 and a central axis of the tubular distal side connection portion 26 extend in the same direction and a center axis of the male connector connection port P23 is disposed to be perpendicular to such a direction.

The medical connector 2 is constituted by a proximal side housing h21 made of, for example, resin, a distal side housing h22 made of, for example, resin, and a valve member v2 made of, for example, rubber in the present embodiment. The proximal side housing h21 and the distal side housing h22 are joined to each other with the valve member v2 sandwiched therebetween.

The proximal side connection portion 25 and the male connector connection portion 23 described above are configured using the proximal side housing h21. In addition, the distal side connection portion 26 and the male connector housing portion 24 are configured using the distal side housing h22. In addition, the body member 21 is constituted by the proximal side housing h21 and the distal side housing h22. Further, the valve body 22 and the check valve 27 are configured using the valve member v2. In this manner, the check valve 27 is integrally formed with the valve body 22 which closes the male connector connection port P23.

When being used in the infusion device, the medical connector 2 configured as described above can operate as follows. First, the check valve 27 is opened by the pressure of the fluid on the proximal side positioned on an infusion container side as illustrated in FIG. 6 at the time of supplying the fluid to the living body, and thus, the fluid can flow from the proximal side opening P21 to the distal side opening P22 through the flow path R2. Therefore, it is possible to supply the fluid from the infusion container to the living body through the medical connector 2.

In addition, even if the pressure of the fluid on the distal side positioned on the living body side is increased as illustrated in FIG. 7 at the time of stopping the supply of the fluid to the living body, this pressure is applied in a direction to close the check valve 27, and thus, the inflow of the fluid from the male connector housing portion 24 to the proximal side opening P21 is prevented. Therefore, occurrence of reverse flow of the fluid from the living body into the infusion device is prevented at the time of stopping the supply of the fluid, safety is secured, and occurrence of occlusion in the infusion device is prevented.

Further, when a medical device such as a syringe is prepared for fluid collection and the male connector C connected to this medical device is connected to the male connector connection portion 23 at the time of collecting the fluid from the living body as illustrated in FIG. 8, the communicating hole 24a is closed by an outer peripheral surface of the distal end portion C1 of the male connector C. In addition, even if the male connector C is inserted until the distal end surface C1a abuts the step portion 24b at this time, the communicating state between the male connector C and the distal side opening P22 is secured via a gap adjacent to the step portion 24b. Therefore, it is possible to collect the fluid only from the living body by preventing the inflow of the fluid from the infusion container.

As described above, the medical connector 2 of the present embodiment is configured such that the male connector C communicates with the distal side opening P22 and the inflow of the fluid from the proximal side opening P21 to the male connector housing portion 24 is prevented by the connection of the male connector C to the male connector connection portion 23, and thus, it is possible to start collecting the fluid only by connecting the male connector C to the male connector connection portion 23 and to facilitate the collection of the fluid into the male connector C.

In addition, the medical connector 2 of the present embodiment is configured such that the communicating hole 24a is closed by the male connector C connected to the male connector connection portion 23, and thus, it is possible to facilitate the collection of the fluid into the male connector C with the simple configuration.

In addition, since the check valve 27 is provided between the communicating hole 24a and the proximal side opening P21 in the medical connector 2 of the present embodiment, it is also possible to prevent occurrence of reverse flow of the fluid from the living body.

In addition, the medical connector 2 of the present embodiment realizes simplification of the configuration and an assembly process by integrally forming the valve body 22 and the check valve 27.

Next, a medical connector 3 according to still another embodiment of the present invention will be illustrated and described in detail with reference to FIGS. 9 to 11.

Figure 9:
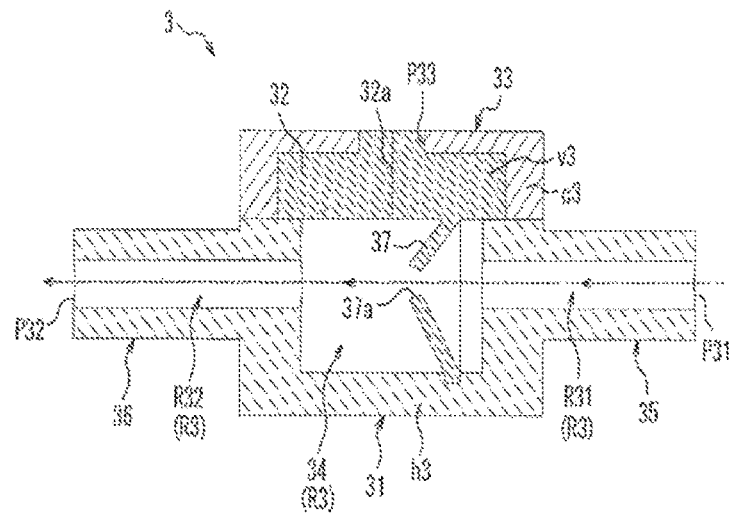
FIG. 9 is a cross-sectional view illustrating a state at the time of supplying a fluid to a living body when a medical connector according to still another embodiment of the present invention is used in the infusion device.
Figure 10:
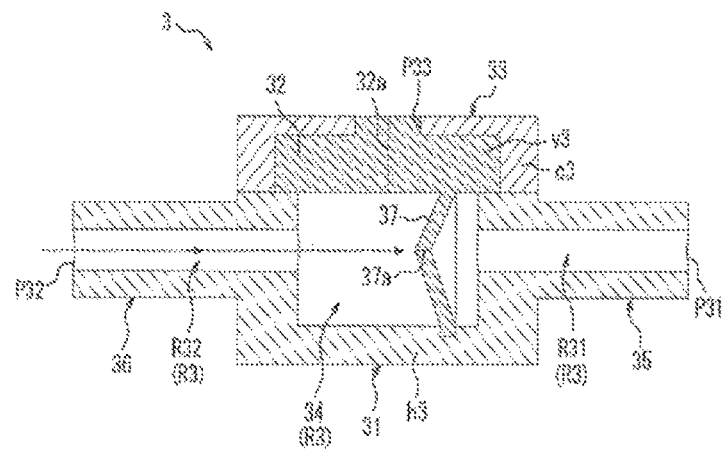
FIG. 10 is a cross-sectional view illustrating a state at the time of stopping supply of a fluid to a living body when the medical connector of FIG. 9 is used in the infusion device.
Figure 11:
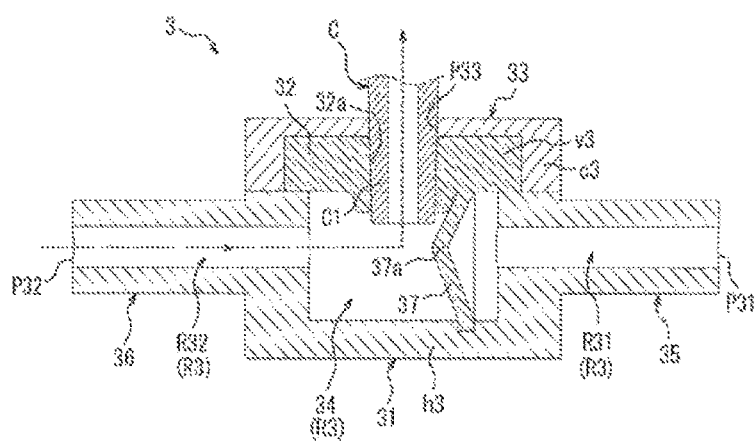
FIG. 11 is a cross-sectional view illustrating a state at the time of collecting a fluid from a living body when the medical connector of FIG. 9 is used in the infusion device.

FIGS. 9 to 11 illustrate states in the case of using the medical connector 3 of the present embodiment in an infusion device that supplies a fluid to a living body. FIG. 9 illustrates the state at the time of supplying a fluid to the living body, FIG. 10 illustrates the state at the time of stopping supply of a fluid to the living body, and FIG. 11 illustrates the state at the time of collecting a fluid from the living body.

The medical connector 3 of the present embodiment has the same configuration as that of the embodiment described with reference to FIGS. 1 to 4, except for configurations of a male connector housing portion 34 and a check valve 37.

The male connector housing portion 34 has an inner peripheral surface having a bottomed cylindrical shape. In addition, the male connector housing portion 34 is provided with the check valve 37 which has a slit 37a having a straight-line shape, and is configured as a duckbill valve that allows inflow of the fluid from a proximal side opening P31 to a male connector housing portion 34 via the slit 37a. That is, the check valve 37 is provided in a flow path R3 between a male connector connection port P33 and the proximal side opening P31. In addition, the straight-line shaped slit 37a of the check valve 37 extends to be substantially perpendicular with respect to a center axis line of the male connector connection port P33. Further, the check valve 37 is integrally formed with the valve body 32 which closes the male connector connection port P33.

When being used in the infusion device, the medical connector 3 configured as described above can operate as follows. First, the check valve 37 is opened by the pressure of the fluid on the proximal side positioned on the infusion container side as illustrated in FIG. 9 at the time of supplying the fluid to the living body, and thus, the fluid can flow from the proximal side opening P31 to a distal side opening P32 through the flow path R3. Therefore, it is possible to supply the fluid from an infusion container to the living body through the medical connector 3.

In addition, even if the pressure of the fluid on the distal side positioned on the living body side is increased as illustrated in FIG. 10 at the time of stopping the supply of the fluid to the living body, this pressure is applied in a direction to close the check valve 37, and thus, the inflow of the fluid from the male connector housing portion 34 to the proximal side opening P31 is prevented. Therefore, occurrence of reverse flow of the fluid from the living body into the infusion device is prevented at the time of stopping the supply of the fluid, safety is secured, and occurrence of occlusion in the infusion device is prevented.

Further, when a medical device such as a syringe is prepared for fluid collection and a male connector C connected to this medical device is connected to the male connector connection portion 33 at the time of collecting the fluid from the living body as illustrated in FIG. 11, the male connector C communicates with the distal side opening P32, and a pressing force from the male connector C is applied in a direction to close the check valve 37, so that the inflow of the fluid from the proximal side opening P31 to the male connector housing portion 34 is prevented. Therefore, it is possible to collect the fluid only from the living body by preventing the inflow of the fluid from the infusion container.

Incidentally, the medical connector 3 of the present embodiment is configured such that the check valve 37 prevents the inflow of the fluid by abutting on a portion of the valve body 32 pushed into the male connector C, but the check valve 37 may be configured to prevent the inflow of the fluid by abutting on a distal end portion C1 of the male connector C.

As described above, the medical connector 3 of the present embodiment is configured such that the male connector C communicates with the distal side opening P32 and the inflow of the fluid from the proximal side opening P31 to the male connector housing portion 34 is prevented by the connection of the male connector C to the male connector connection portion 33, and thus, it is possible to start collecting the fluid only by connecting the male connector C to the male connector connection portion 33 and to facilitate the collection of the fluid into the male connector C.

In addition, the medical connector 3 of the present embodiment is configured such that the check valve 37 is provided in the male connector housing portion 34, and the check valve 37 prevents the inflow of the fluid from the proximal side opening P31 to the male connector housing portion 34, by the pressing force from the male connector C connected to the male connector connection portion 33, and thus, it is possible to prevent the reverse flow of the fluid from the living body by the check valve 37 and to facilitate the collection of the fluid into the male connector C.

In addition, the medical connector 3 of the present embodiment is configured such that the check valve 37 has the slit 37a and allows the inflow of the fluid from the proximal side opening P31 to the male connector housing portion 34 via the slit 37a, and thus, it is possible to prevent the occurrence of reverse flow of the fluid from the living body and to facilitate the collection of the fluid into the male connector C with the simple configuration.

In addition, the medical connector 3 of the present embodiment realizes simplification of the configuration and an assembly process by integrally forming the valve body 32 and the check valve 37.

Incidentally, the medical connector 1 described with reference to FIGS. 1 to 4, the medical connector 2 described with reference to FIGS. 5 to 8, and the medical connector 3 described with reference to FIGS. 9 to 11 are configured as the T-shaped connector, but may be configured as a connector having another configuration, and may be configured as, for example, a Y-shaped connector in which a center axis line of the tubular proximal side connection portion 15, 25, or 35 and a center axis line of the tubular distal side connection portion 16, 26, or 36 extend in different directions, and a center axis line of the male connector connection port P13, P23, or P33 is disposed in substantially the same direction as the center axis line of the tubular distal side connection portion 16, 26, or 36. In addition, it may be configured as a connector equipped with an indwelling needle including an indwelling needle instead of the distal side connection portions 16, 26, and 36. Further, it is also possible to form the proximal side connection portions 15, 25, and 35 as closed female connectors or to form the distal side connection portions 16, 26, and 36 as male luer.

Next, an infusion set 100 according to one embodiment of the present invention will be illustrated and described in detail with reference to FIG. 12.

Figure 12:
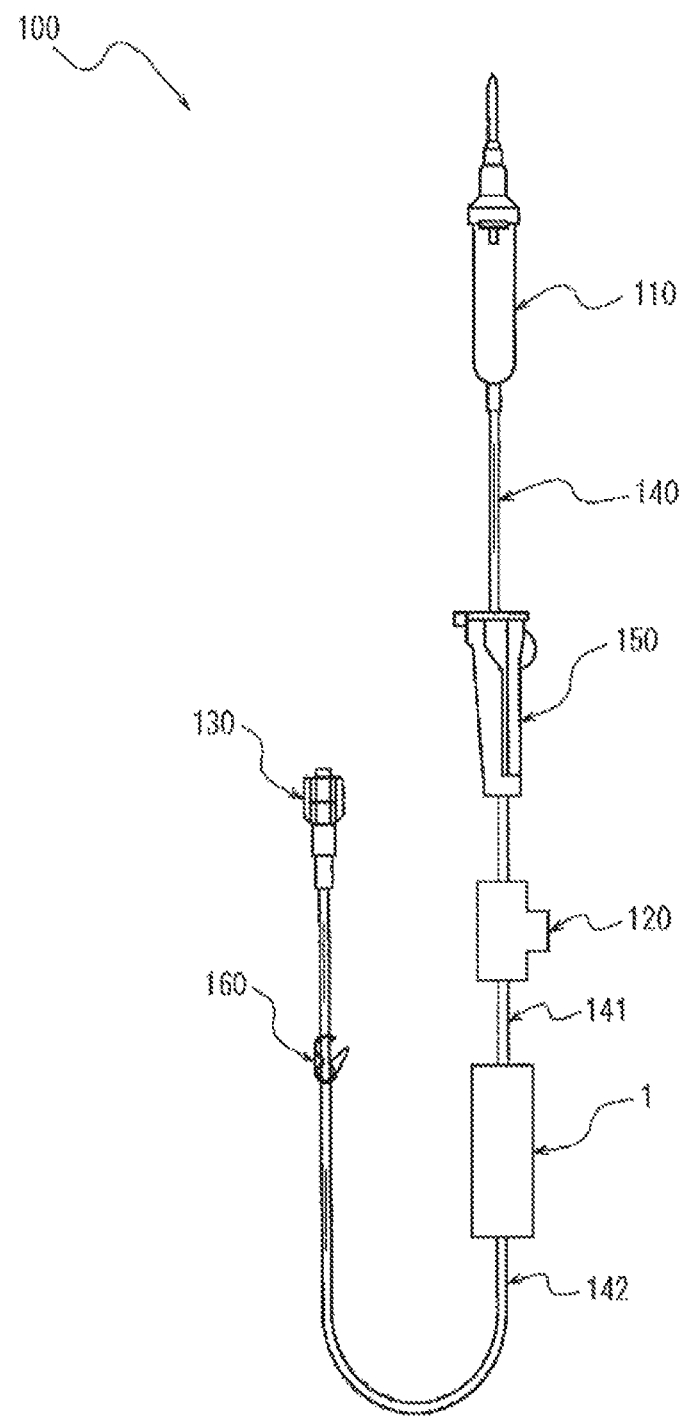
FIG. 12 is an overall view illustrating an infusion set according to one embodiment of the present invention.

As illustrated in FIG. 12, the infusion set 100 of the present embodiment is formed of a plurality of parts to constitute a part or the whole of an infusion device that supplies a fluid such as a medical solution and a saline solution to a living body such as a patient.

In the present embodiment, the infusion set 100 includes: a drip tube 110 that is connected to an infusion container (not illustrated), for example, an infusion bag or the like, which contains the fluid to be supplied to the living body, and enables visual confirmation of a supply amount of the fluid; a connector 120 for mixed injection; the medical connector 1 described with reference to FIGS. 1 to 4; and a connector 130 for an indwelling needle to be connected to the indwelling needle (not illustrated) that is indwelled in the living body to inject the fluid.

In addition, the infusion set 100 includes: a first tube 140 that connects the drip tube 110 and the connector 120 for mixed injection; a second tube 141 that connects the connector 120 for mixed injection and the medical connector 1; and a third tube 142 that connects the medical connector 1 and the connector 130 for an indwelling needle.

Further, the infusion set 100 includes: a flow rate adjustment clamp (for example, a roller clamp) 150 attached to the first tube 140 in order to adjust the supply amount of the fluid; and a one-touch clamp 160 attached to the third tube 142 in order to enable stop of the supply of the fluid.

In this manner, the infusion set 100 of the present embodiment includes the drip tube 110, the connector 120 for mixed injection, the medical connector 1, the connector 130 for an indwelling needle, the first tube 140, the second tube 141, the third tube 142, the flow rate adjustment clamp 150, and the one-touch clamp 160 as the parts to form the infusion device.

The infusion set 100 may include the infusion container or the indwelling needle. In addition, the infusion set 100 may include, for example, an air filter configured to remove air in the infusion device, a filter for sterilization, a three-way stopcock, and the like other than the above-described parts. In addition, it is sufficient that the infusion set 100 includes a plurality of parts including the medical connector 1, and one or a plurality of the above-described parts may be omitted.

As described above, since the infusion set 100 of the present embodiment includes the medical connector 1, it is possible to facilitate collection of the fluid into the male connector C (see FIG. 4) at the time of performing infusion into the living body, and it is possible to reduce risks such as reverse flow of blood from the living body and blood removal.

It is preferable to form the infusion set 100 of the present embodiment such that the medical connector 1 is disposed on the downstream side of the infusion device in order to further reduce the risks such as the reverse flow of blood from the living body and the blood removal at the time of performing the infusion into the living body.

In addition, the infusion set 100 of the present embodiment may be configured to include at least one of the medical connector 2 described with reference to FIGS. 5 to 8, the medical connector 3 described with reference to FIGS. 9 to 11, or the above-described modified example of the medical connectors 1 to 3 in place of or in addition to the medical connector 1.

Next, a fluid collection method according to one embodiment of the present invention will be illustrated and described in detail.

The fluid collection method of the present embodiment is configured to collect a fluid from a flow path of a medical connector including a body member that partitions the flow path between a proximal side opening and a distal side opening; and a male connector connection portion that has a male connector connection port which can be opened and closed by a valve body facing the flow path.

Further, the fluid collection method of the present embodiment includes the steps of: connecting a male connector to the male connector connection portion; causing the male connector to communicate with a distal side opening and preventing inflow of the fluid from a proximal side opening to the male connector by the connection of the male connector to the male connector connection portion; and collecting the fluid from the distal side opening to the male connector.

Therefore, according to the fluid collection method of the present embodiment, it is possible to start collecting the fluid only by connecting the male connector to the male connector connection portion, and thus, it is possible to facilitate the collection of the fluid into the male connector.

In addition, the fluid collection method of the present embodiment can include a step of stopping the supply of the fluid from the proximal side opening to the distal side opening and a step of preventing reverse flow of the fluid from the distal side opening to the proximal side opening using a check valve before the step of connecting the male connector to the male connector connection portion. Further, the fluid collection method of the present embodiment can include a step of causing the male connector to communicate with the distal side opening by the connection of the male connector to the male connector connection portion and preventing the inflow of the fluid from the proximal side opening to the male connector by pressing the check valve with the male connector to maintain a closed state of the check valve instead of the step of causing the male connector to communicate with the distal side opening and preventing the inflow of the fluid from the proximal side opening to the male connector by the connection of the male connector to the male connector connection portion.

In the fluid collection method according to such a modified example, it is possible to prevent the reverse flow of the fluid at the time of stopping the supply of the fluid and to facilitate the collection of the fluid into the male connector.

The above description merely illustrates exemplary embodiments of the present invention, and it should be understood that various modifications can be made to those embodiments while remaining within the scope of the claims.

REFERENCE NUMERAL LIST 1 medical connector
11 body member
12 valve body
12a slit
13 male connector connection portion
14 male connector housing portion
14a valve seat
15 proximal side connection portion
16 distal side connection portion
17 check valve
P11 proximal side opening
P12 distal side opening
P13 male connector connection port
R1 flow path
R11 proximal side flow path
R12 distal side flow path
h1 housing
c1 cap
v1 valve member
2 medical connector
21 body member
22 valve body
22a slit
23 male connector connection portion
24 male connector housing portion
24a communicating hole
24b step portion
25 proximal side connection portion
26 distal side connection portion
27 check valve
27a slit
P21 proximal side opening
P22 distal side opening
P23 male connector connection port
R2 flow path
R21 proximal side flow path
R22 distal side flow path
h21 proximal side housing
h22 distal side housing
v2 valve member
3 medical connector
31 body member
32 valve body
32a slit
33 male connector connection portion
34 male connector housing portion
35 proximal side connection portion
36 distal side connection portion
37 check valve
37a slit
P31 proximal side opening
P32 distal side opening
P33 male connector connection port
R3 flow path
R31 proximal side flow path
R32 distal side flow path
h3 housing
c3 cap
v3 valve member
C male connector
C1 distal end portion of male connector
C1a distal end surface of male connector
100 infusion set
110 drip infusion cylinder
120 connector for mixed injection
130 connector for indwelling needle
140 first tube
141 second tube
142 third tube
150 flow rate adjustment clamp
160 one touch clamp

What is claimed is:

1. A medical connector comprising:
a body member that partitions a flow path between a proximal side opening and a distal side opening, wherein the body member comprises a male connector housing portion comprising a valve seat; and
a male connector connection portion comprising:
a valve body facing the flow path, and
a male connector connection port openable and closable by the valve body;
an elastic check valve located in the male connector housing portion and configured to seat on the valve seat,
wherein the male connector housing portion is configured to house a distal end portion of a male connector connected to the male connector connection portion, and
wherein the male connector housing portion is configured such that, when the male connector is connected to the male connector connection portion, the male connector housing portion (i) causes the male connector to communicate with the distal side opening and (ii) prevents inflow of a fluid from the proximal side opening to the male connector housing portion,
wherein the check valve is configured such that, when the male connector is not connected to the male connector connection portion, the check valve (i) allows inflow of the fluid from the proximal side opening to the male connector housing portion via a space between the valve seat and the check valve, and (ii) prevents inflow of the fluid from the male connector housing portion to the proximal side opening, and
wherein the check valve is configured such that, when the male connector is connected to the male connector connection portion, the check valve prevents inflow of the fluid from the proximal side opening to the male connector housing portion by a pressing force from the male connector.

2. The medical connector according to claim 1, wherein the valve body and the check valve are integrally formed.

3. An infusion set comprising the medical connector according to claim 1.

4. A medical connector comprising:
a body member that partitions a flow path between a proximal side opening and a distal side opening, wherein the body member comprises a male connector housing portion comprising a communicating hole; and
a male connector connection portion comprising:
a valve body facing the flow path, and
a male connector connection port openable and closable by the valve body,
wherein the body member comprises a male connector housing portion configured to house a distal end portion of a male connector connected to the male connector connection portion, and
wherein the male connector housing portion is configured such that, when the male connector is not connected to the male connector connection portion, the communicating hole causes the male connector housing portion and the proximal side opening to communicate with each other, wherein the male connector housing portion is configured such that, when the male connector is connected to the male connector connection portion, the male connector housing portion (i) causes the male connector to communicate with the distal side opening, and (ii) prevents inflow of a fluid from the proximal side opening to the male connector housing portion by the communicating hole being closed by the male connector.

5. The medical connector according to claim 4, further comprising:
a check valve that is located between the communicating hole and the proximal side opening,
wherein the check valve is configured such that, when the male connector is not connected to the male connector connection portion, the check valve (i) allows inflow of the fluid from the proximal side opening to the communicating hole, and (ii) prevents inflow of the fluid from the communicating hole to the proximal side opening.

6. The medical connector according to claim 5, wherein the check valve has a slit and is configured such that, when the male connector is not connected to the male connector connection portion, the check valve allows inflow of the fluid from the proximal side opening to the male connector housing portion via the slit.

7. The medical connector according to claim 5, wherein the valve body and the check valve are integrally formed.

8. An infusion set comprising the medical connector according to claim 4.

* * * * *